US00PP35542P2

(12) United States Plant Patent
von Tubeuf

(10) Patent No.: US PP35,542 P2
(45) Date of Patent: Dec. 12, 2023

(54) POINSETTIA PLANT NAMED 'NPCW22279'

(50) Latin Name: *Euphorbia pulcherrima*
Varietal Denomination: NPCW22279

(71) Applicant: KLEMM + SOHN GMBH & CO. KG, Stuttgart (DE)

(72) Inventor: Guido von Tubeuf, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/084,823

(22) Filed: Dec. 20, 2022

(51) Int. Cl.
*A01H 5/12* (2018.01)
*A01H 6/38* (2018.01)

(52) U.S. Cl.
USPC ..... Plt./307

(58) Field of Classification Search
USPC ..... Plt./307
CPC ... A01H 5/02; A01H 5/12; A01H 5/00; A01H 6/38; A01H 6/385
See application file for complete search history.

(56) References Cited

U.S. PATENT DOCUMENTS

PP19,022 P2 * 7/2008 Arts ..... A01H 5/02 Plt./307

OTHER PUBLICATIONS

Adam PennState Extension Poinsettias—What's New with this Old Plant, retrieved on Mar. 1, 2023 at https://extension.psu.edu/poinsettias-whats-new-with-this-old-plant, 2021, 2 pp. (Year: 2021).*
Selecta One Poinsettias 2022 retrieved on Mar. 1, 2023 at https://www.ballseed.com/PDF/Catalogs/Poinsettia2022_Catalog_SEL_211810828.pdf, cover page, 1 introductory page, pp. 1-2, 30 and 48. (Year: 2022).*

* cited by examiner

*Primary Examiner* — June Hwu
(74) *Attorney, Agent, or Firm* — Weatherly IP Solutions, LLC; James M. Weatherly

(57) ABSTRACT

A new poinsettia plant particularly distinguished by having a more upright plant habit, medium vigor and red bracts, is disclosed.

1 Drawing Sheet

Genus and species: *Euphorbia pulcherrima.*
Variety denomination: 'NPCW22279'.

BACKGROUND OF THE NEW PLANT

The present invention comprises a new and distinct variety of poinsettia, botanically known as *Euphorbia pulcherrima* and hereinafter referred to by the variety name 'NPCW22279'. 'NPCW22279' is a selection from a controlled cross conducted in December 2012 in Stuttgart, Germany of the proprietary female *Euphorbia* line 'NPCW08135' (unpatented) and the proprietary male *Euphorbia* line 'NPCW12200' (U.S. Plant Pat. No. 25,049). Seeds from the cross were selected and plants were grown for evaluation. A plant line was selected in November 2013 in Stuttgart, Germany and named 'NPCW22279'. In May 2014, 'NPCW22279' was first vegetatively propagated by apical cuttings. 'NPCW22279' was found to reproduce true to type in successive generations of asexual propagation via apical cuttings in Stuttgart, Germany.

SUMMARY

The following are the most outstanding and distinguishing characteristics of this new variety when grown under normal horticultural practices in Stuttgart, Germany.

1. Medium vigor; and
2. More upright plant growth habit.

DESCRIPTION OF THE PHOTOGRAPH

This new poinsettia plant is illustrated by the accompanying photograph which shows an overall view of the plant.

The photograph is of a plant approximately fourteen-weeks-old, grown indoors in Borgo Bainsizza, Italy in November 2022. The colors shown are as true as can be reasonably obtained by conventional photographic procedures.

DESCRIPTION OF THE NEW VARIETY

The following detailed descriptions set forth the distinctive characteristics of 'NPCW22279'. The data which define these characteristics were collected from asexual reproductions carried out in Borgo Bainsizza, Italy. Data was collected on fourteen-week-old plants grown indoors in Borgo Bainsizza, Italy under greenhouse conditions in November of 2022. Color references are to The R.H.S. Colour Chart of The Royal Horticultural Society of London (R.H.S.), 5$^{th}$ edition (2007).

Classification:
*Family.*—Euphorbiaceae.
*Species.*—*Euphorbia pulcherrima.*
*Common name.*—Poinsettia.
*Variety.*—'NPCW22279'.

Parentage:
*Male.*—*Euphorbia* line 'NPCW12200' (U.S. Plant Pat. No. 25,049).
*Female.*—*Euphorbia* line 'NPCW08135' (unpatented).

Plant:
*Form.*—Triangular.
*Growth habit.*—Upright.
*Height.*—41.0 cm.
*Width.*—59.0 cm.

*Average number of inflorescences per plant.*—5.0.
*Keeping quality.*—Very Good.
*Time to produce a cutting.*—5 to 6 weeks.
*Flowering response time.*—Approximately 50 days.

Propagation:
*Type cuttings.*—Apical cuttings.
*Rooting habit and root color.*—Freely branching and RHS NN155C (White).

Lateral branches:
*Color.*—RHS 143C.
*Length.*—31.0 cm.
*Internode length.*—2.0 to 4.0 cm.
*Diameter.*—0.4 cm to 0.6 cm.
*Branching habit.*—Freely branching.
*Number of lateral branches per plant.*—5.
*Texture.*—Smooth.
*Strength.*—Strong.
*Stem anthocyanin.*—Present with slight intensity.

Leaves:
*Quantity.*—8 to 10 per lateral branch.
*Arrangement.*—Alternate.
*Number of lobes on the leaf blade.*—0, almost entire.
*Lobation depth.*—Almost entire.
*Depth of the deepest sinus of the leaf blade.*—0.2 cm.
*Shape.*—Obtuse.
*Apex.*—Acuminate.
*Base.*—Rounded.
*Margin.*—Almost entire.
*Length.*—13.0 cm to 15.0 cm.
*Width.*—7.0 cm to 9.0 cm.
*Texture.*—Upper surface: Smooth. Lower surface: Slightly pubescent.
*Vein color.*—Upper surface: The veins are transparent but show the yellow green color of the leaf. Lower surface: RHS 145C.
*Variegation.*—Absent.
*Venation pattern.*—Reticulate.
*Color.*—Mature foliage: Upper surface: Closest to RHS 139A. Lower surface: RHS N138B. Immature foliage: Upper surface: RHS 138A. Lower surface: RHS 137C.
*Leaf petiole.*—Length: 4.0 cm to 6.0 cm. Diameter: 0.2 cm to 0.3 cm. Color: Upper (part) surface: RHS 181B. Lower (part) surface: RHS 182C. Texture: Smooth. Strength: Strong. Transitional leaves: No. Petiole lower side intensity of the anthocyanin coloration: Moderate.

Inflorescence:
*Type and habit.*—Cluster of cyathia surrounded by bracts.
*Quantity per lateral branch.*—1.
*Position relative to foliar plane.*—Above.
*Lastingness of inflorescence on the plant.*—4 to 5 weeks.
*Natural flowering season.*—November.
*Diameter.*—27.0 cm to 28.0 cm.
*Height.*—2.0 cm to 3.0 cm.
*Fragrance.*—Absent.

Bracts:
*Number of bracts per inflorescence.*—10 to 11.
*Shape.*—Obtuse.
*Apex.*—Acuminate.
*Base.*—Rounded.
*Margin.*—Entire.
*Size.*—Length: 9.0 cm to 14.0 cm. Width: 6.0 cm to 10.0 cm.
*Texture (both upper and lower surfaces).*—Smooth.
*Folding along the main vein.*—Absent.
*Twisting.*—Absent.
*Rugosity between the veins.*—Weak.
*Venation pattern.*—Reticulate.
*Vein color.*—Upper surface: RHS 59B. Lower surface: RHS 181B.
*Bract color.*—Upper surface: RHS 46C. Lower surface: RHS 53B.
*Bract petiole.*—Length: 0.5 cm to 1.5 cm. Diameter: 0.2 cm. Color: Upper (part) surface: RHS 59A. Lower (part) surface: RHS 181B. Texture: Smooth. Strength: Medium.

Cyme:
*Diameter.*—2.5 cm to 3.0 cm.
*Cyathia number.*—8.0 cm to 10.0 cm per inflorescence.
*Deformation of glands of the cyathium.*—Absent.
*Timing of opening of cyathia.*—Opens mid-November; first pollen appears in parallel to opening of the nectar cups, stigmas appear 2 weeks later.
*Cyathium.*—Shape: Ovate. Texture: Smooth. Diameter: 0.3 cm to 0.7 cm. Length: 0.3 cm to 0.8 cm. Color: RHS 143C.
*Peduncle.*—Color: RHS 142B. Length: 0.2 cm. Diameter: 0.1 cm. Texture: Smooth. Strength: Medium.
*Nectar cups.*—Number: 1 per cyathium. Diameter: 0.1 cm. Length: 0.3 cm to 0.4 cm. Color: RHS 11A to RHS 33B. Shape: Lip shaped. Texture: Smooth.

Reproductive organs:
*Stamen quantity.*—10-15 per cyathium.
*Stamen shape.*—Ovate.
*Filament length.*—0.25 cm.
*Filament color.*—RHS 46A.
*Pollen quantity.*—Moderate.
*Pollen color.*—12A.
*Gynoecium.*—Not observed.

Fruit and seed set: Not observed.

Disease and insect resistance: No particular disease or insect resistance observed.

COMPARISON WITH PARENTAL LINE AND KNOWN VARIETY

'NPCW22279' is distinguished from its mutation parent as described in Tables 1a and 1b:

TABLE 1a

Comparison with Female Parental Line

| Trait or characteristic | Instant variety 'NPCW22279' | Female parent 'NPCW08135' |
|---|---|---|
| Plant habit | More upright | Wider |
| Leaf shape | Obtuse | Lobed |
| Bract color | Upper surface: RHS 46C Lower surface: RHS 53B | Upper surface: RHS 45A. Lower surface: RHS 46C-D. |

TABLE 1b

| Comparison with Male Parental Line | | |
|---|---|---|
| Trait or characteristic | Instant variety 'NPCW22279' | Male Parent 'NPCW12200' |
| Vigour | Medium | Low |
| Plant habit | More upright | Wider |
| Bract color | Upper surface: RHS 46C Lower surface: RHS 53B | Upper surface: RHS 45A and RHS 45B. Lower surface: RHS 47B. |
| Leaf shape | Obtuse | Ovate |
| Leaf apex | Acuminate | Acute |

COMPARISON WITH SIMILAR VARIETY

'NPCW22279' is most similar to the commercial poinsettia plant named 'Premium Red' (unpatented). Differences between the two varieties are described in Table 2:

TABLE 2

| Trait | Variety 'NPCW22279' | Commercial line 'Premium Red' |
|---|---|---|
| Vigour | Medium | Low |
| Leaf size | Wider than 'Premium Red' | Narrower than 'NPCW22279' |
| Bract size | Wider than 'Premium Red' | Narrower than 'NPCW22279' |

I claim:

1. A new and distinct cultivar of Poinsettia Plant Named 'NPCW22279' as described and illustrated herein.

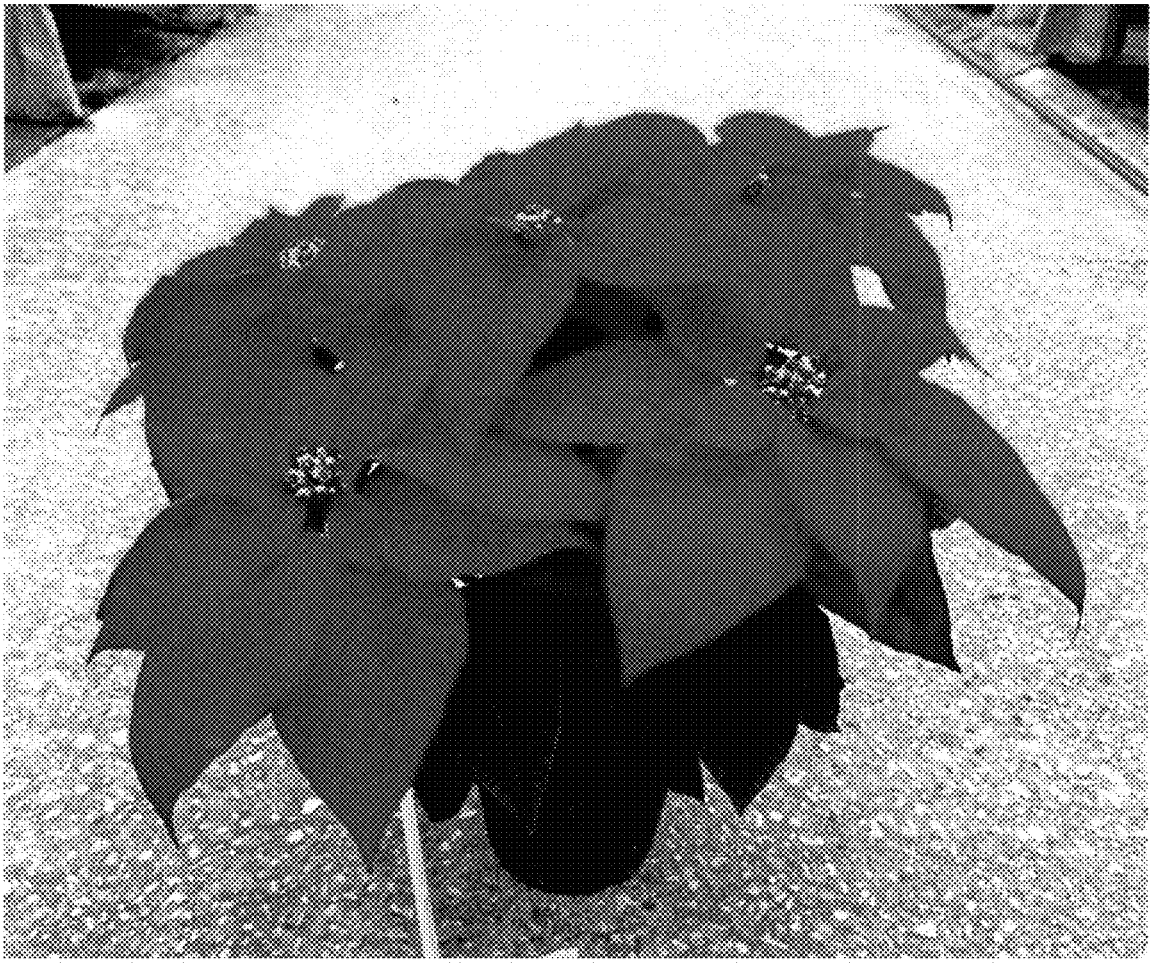

* * * * *